United States Patent
Moriarty et al.

(10) Patent No.: US 9,980,647 B2
(45) Date of Patent: *May 29, 2018

(54) UNLOCKING A BODY AREA NETWORK

(71) Applicant: QUALCOMM Incorporated, San Diego, CA (US)

(72) Inventors: Anthony Moriarty, Roseville (AU); Jessica M. Flanagan, Ashfield (AU); Cameron A. McDonald, Queenscliff (AU)

(73) Assignee: QUALCOMM Incorporated, San Diego, CA (US)

( * ) Notice: Subject to any disclaimer, the term of this patent is extended or adjusted under 35 U.S.C. 154(b) by 486 days.

This patent is subject to a terminal disclaimer.

(21) Appl. No.: 14/868,538

(22) Filed: Sep. 29, 2015

(65) Prior Publication Data

US 2016/0015270 A1 Jan. 21, 2016

Related U.S. Application Data

(63) Continuation of application No. 13/360,469, filed on Jan. 27, 2012, now Pat. No. 9,186,071.

(51) Int. Cl.
| | | |
|---|---|---|
| *G08B 1/08* | (2006.01) | |
| *A61B 5/00* | (2006.01) | |
| *G06F 19/00* | (2018.01) | |
| *A61B 5/0205* | (2006.01) | |
| *G06F 21/62* | (2013.01) | |
| *H04W 12/08* | (2009.01) | |

(52) U.S. Cl.
CPC .......... *A61B 5/0024* (2013.01); *A61B 5/0022* (2013.01); *A61B 5/02055* (2013.01); *A61B 5/747* (2013.01); *A61B 5/7475* (2013.01); *G06F 19/3418* (2013.01); *G06F 21/6245* (2013.01); *G16H 50/20* (2018.01); *H04W 12/08* (2013.01); *A61B 2560/0266* (2013.01)

(58) Field of Classification Search
CPC .......................... G06F 19/3418; A61B 5/0002
USPC ........................ 340/539.12–539.13; 705/2, 3
See application file for complete search history.

(56) References Cited

U.S. PATENT DOCUMENTS

| | | |
|---|---|---|
| 7,733,224 B2 | 6/2010 | Tran |
| 2006/0282649 A1 | 12/2006 | Malamud et al. |

(Continued)

FOREIGN PATENT DOCUMENTS

| | | |
|---|---|---|
| CN | 101268930 A | 9/2008 |
| CN | 201469259 U | 5/2010 |

(Continued)

OTHER PUBLICATIONS

Gupta et al. "Ensuring Safety, Sustainability, and Security in Body Area Networks," 2010 Wireless Symposium and Summer School, Virginia Tech. Jun. 2010 pp. 95-107.

(Continued)

*Primary Examiner* — Ojiako Nwugo
(74) *Attorney, Agent, or Firm* — Kilpatrick Townsend & Stockton LLP (57) ABSTRACT

Disclosed is an apparatus, system, and method to unlock a body area network (BAN) of a patient and to transmit medical data about the patient. The BAN, under the control of a body area controller (BAC), may be unlocked based upon a pre-defined patient action performed by the patient and the BAN may then be connected to a wireless device. The BAN medical data of the patient may then be transmitted by the wireless device.

21 Claims, 6 Drawing Sheets

(56) References Cited

U.S. PATENT DOCUMENTS

| | | |
|---|---|---|
| 2007/0249288 A1 | 10/2007 | Moallemi et al. |
| 2008/0154098 A1 | 6/2008 | Morris et al. |
| 2008/0287748 A1 | 11/2008 | Sapounas |
| 2009/0037224 A1 | 2/2009 | Raduchel |
| 2009/0040041 A1 | 2/2009 | Janetis et al. |
| 2009/0069642 A1 | 3/2009 | Gao et al. |
| 2009/0097224 A1 | 4/2009 | Drye |
| 2009/0318779 A1 | 12/2009 | Tran |
| 2010/0028658 A1 | 2/2010 | Nagasawa et al. |
| 2010/0298658 A1 | 11/2010 | McCombie et al. |
| 2011/0018731 A1 | 1/2011 | Linsky et al. |
| 2011/0063105 A1 | 3/2011 | Bennett et al. |
| 2011/0066010 A1 | 3/2011 | Moon et al. |
| 2011/0197067 A1 | 8/2011 | Corndorf |
| 2011/0201898 A1 | 8/2011 | Benco et al. |
| 2011/0282671 A1 | 11/2011 | Dicks et al. |
| 2012/0001751 A1 | 1/2012 | Baker et al. |
| 2012/0254987 A1 | 10/2012 | Ge et al. |
| 2013/0041290 A1 | 2/2013 | Kording et al. |
| 2013/0194092 A1 | 8/2013 | Moriarty et al. |

FOREIGN PATENT DOCUMENTS

| | | |
|---|---|---|
| WO | 2005122879 A1 | 12/2005 |
| WO | WO-2007060560 A1 | 5/2007 |
| WO | WO-2007060650 A1 | 5/2007 |
| WO | 2007121334 A2 | 10/2007 |
| WO | 2009127954 A2 | 10/2009 |
| WO | 2010023962 A1 | 3/2010 |
| WO | 2010100013 A1 | 9/2010 |
| WO | 2010100442 A1 | 9/2010 |
| WO | 2011039745 A1 | 4/2011 |
| WO | WO-2011133799 A1 | 10/2011 |
| WO | 2012117320 A1 | 9/2012 |

OTHER PUBLICATIONS

International Search Report and Written Opinion—PCT/US2013/023348—ISA/EPO—dated Jun. 18, 2013.

UNLOCKING A BODY AREA NETWORK

CROSS-REFERENCE TO RELATED APPLICATIONS

This application is a continuation application of, and claims the benefit of priority to, U.S. patent application Ser. No. 13/360,469, filed on Jan. 27, 2012, the entire contents of which are incorporated herein by reference.

BACKGROUND

Field

The present invention relates generally to an apparatus, system, and method to unlock a body area network (BAN).

Relevant Background

In today's high technology health care environment, systems containing body sensor units (BSUs) are currently utilized for collecting and transmitting physiological data (e.g., vital signs such as blood pressure, pulse rate, etc.), which reflect the health status of a patient. Such systems are commonly referred to as body area networks (BANs). If wireless communication is employed in the system, it may be referred to as a wireless body area network (WBAN). WBANs have been used to wirelessly monitor the health of patients who need frequent monitoring.

Although BANs have become very useful in health care in monitoring the health status of patients, security issues involving access to BANs have not been adequately addressed. One primary concern is how to best control access to a patient's medical data from a patient's BAN, especially in an emergency situation. Based upon present health care security implementations, either there is very little security, causing privacy to be at risk, or, too many security implementations are involved, risking patient safety.

Therefore, as BANs become more prevalent, techniques are needed for emergency workers, as well as other health care professionals, to gain access to the medical information from BANs, as quickly as possible, especially in emergency situations. However, at the same time, great security concerns are present if every emergency worker (or other health care professional) always has available access to every BAN in which case BAN systems are very insecure. Therefore, techniques are needed for proper security in unlocking BANs, so that BAN medical data can be properly utilized by emergency workers and other health care professionals, while still maintaining security for patients.

SUMMARY

In one aspect, a method of unlocking a body area network (BAN) of a patient to transmit medical data is disclosed. The method comprises unlocking the BAN based upon a pre-defined patient action performed by the patient and connecting the BAN to a wireless device. Further, the method comprises transmitting BAN medical data of the patient by the wireless device.

In one aspect, a body area controller (BAC) is disclosed. The BAC may comprise a transceiver and a processor. The processor may unlock a body area network (BAN) based upon a pre-defined patient action performed by a patient and may connect the BAN to a wireless device through the transceiver such that the wireless device is configured to transmit the BAN medical data of the patient.

In one aspect, a body area controller (BAC) is disclosed. The BAC may comprise: means for unlocking a body area network (BAN) based upon a pre-defined patient action performed by a patient; and means for connecting the BAN to a wireless device such that the wireless device is configured to transmit the BAN medical data of the patient.

In one aspect, a computer program product is disclosed that comprises a computer-readable medium including code for: unlocking a body area network (BAN) based upon a pre-defined patient action performed by a patient; and connecting the BAN to a wireless device such that the wireless device is configured to transmit the BAN medical data of the patient.

In one aspect, a method of unlocking a body area network (BAN) of a patient is disclosed. The method comprises unlocking the BAN based upon a pre-defined patient action performed by the patient and connecting the BAN to a wireless device. Further, the method comprises processing information from the BAN using the wireless device.

In one aspect, a method of unlocking a body area network (BAN) of a patient to transmit medical data is disclosed. The method comprises determining if a pre-defined body change of the patient has occurred and/or the patient is incapable of performing a pre-defined patient action and unlocking the BAN automatically. Further, the method comprises connecting the BAN to a wireless device and transmitting BAN medical data of the patient by the wireless device.

In one aspect, a body area controller (BAC) comprising a transceiver and processor is disclosed. The processer determines if a pre-defined body change of the patient has occurred and/or the patient is incapable of performing a pre-defined patient action and unlocks a body area network (BAN). Further, the processor connects the BAN to a wireless device through the transceiver such that the wireless device is configured to transmit the BAN medical data of the patient.

In one aspect a body area controller (BAC) is disclosed that comprises: means for determining if a pre-defined body change of a patient has occurred and/or the patient is incapable of performing a pre-defined patient action and means for unlocking a body area network (BAN). Further, the BAC comprises means for connecting the BAN to a wireless device such that the wireless device is configured to transmit the BAN medical data of the patient.

In one aspect, a computer program product is disclosed that comprises a computer-readable medium including code for: determining if a pre-defined body change of a patient has occurred and/or the patient is incapable of performing a pre-defined patient action; unlocking a body area network (BAN); and connecting the BAN to a wireless device such that the wireless device is configured to transmit the BAN medical data of the patient.

DETAILED DESCRIPTION

The word "example" is used herein to mean "serving as an example, instance, or illustration." Any aspect described herein as an "example" is not necessarily to be construed as preferred or advantageous over other aspects or embodiments.

According to aspects of the invention, a system, method, and apparatus are described in which a body area network (BAN) may be unlocked if a patient is capable of performing a pre-defined patient action (i.e., the patient is conscious) such that the BAN may be unlocked by the patient implementing the pre-defined patient action. An example of this may be a patient pressing against a specific part of the body for a pre-determined period of time or the patient making a specific pre-designated body movement (e.g., touching the backs of the hands together). The actions should be specific enough to ensure that the BAN does not unlock through casual contact and that the patient is aware that they are performing the patient action. However, if the patient is unable to perform the pre-defined patient action (e.g., the patient is unconscious) then the consent to unlock the BAN may be implied (e.g., as with consent for first aid to an emergency worker). Further, if the BAN detects severe body problems (e.g. major heart abnormalities), the BAN may unlock itself on its own accord.

As wireless and mobile devices (e.g., cell phones) are increasingly prevalent, they may be utilized in conjunction with the BAN. For example, a patient's wireless or mobile device (or that of a helpful bystander) may start sending the BAN's medical data to an emergency service (e.g., via x911) when the BAN is unlocked such that the emergency service may send an emergency responder to the patient. Further, this may allow emergency responders (e.g., paramedics) to access the patients' BAN medical data and other health and identity data and prepare while en-route to the patient saving valuable time and this can help medical responders once they arrive. Further, medical advice can be given to the patient and/or helpers while the medical responders are en-route to them.

Figure 1A:
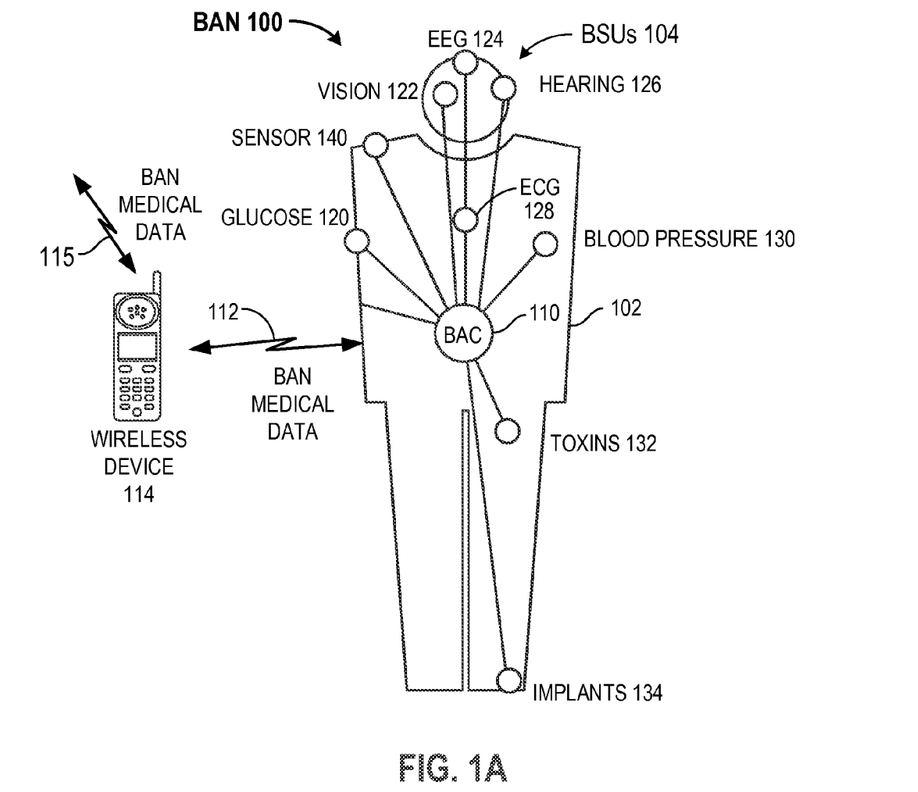
FIG. 1A is a diagram illustrating a BAN system that may be unlocked and connected to a wireless device.
Figure 1B:
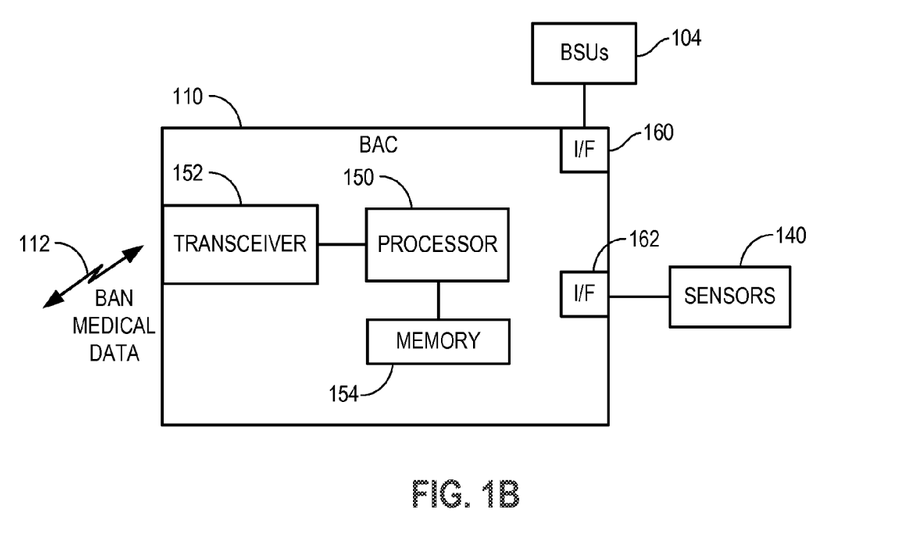
FIG. 1B is a diagram illustrating a BAC of the BAN system.

Aspects of the invention relate to a system, method, and apparatus of unlocking a BAN of a patient to transmit medical data. With reference to FIGS. 1A and 1B, a BAN system 100 is shown that may be unlocked during an emergency situation to transmit medical data about a patient 102 while still ensuring security of the medical data for the patient. BAN 100 may include a plurality of body sensor units (BSUs) 104 coupled to a body area controller (BAC) 110 of the patient 102. BAC 110 may further be wirelessly connected via a link 112 to a wireless or mobile device 114 to transmit BAN medical data about the patient to the wireless or mobile device 114.

As an example, BSUs 104 may include: a glucose monitor 120; a vision monitor 122; an electroencephalography (EEG) monitor 124; a hearing monitor 126; an electrocardiography (ECG) monitor 128; a blood pressure monitor 130; a toxins monitor 132; and implant modules 134. It should be appreciated by those of skill in the art that these are just examples of BSUs that may be utilized in a BAN 100 and that a wide variety of differing types of BSUs may be utilized. Further, as will be described in more detail later, BAN 100 may include sensors 140 that can be used by a patient to unlock the BAN 100 based upon a pre-defined patient action performed by the patient 102.

As shown in FIG. 1B, BAC 110 may include a processor 150 coupled to a transceiver 152 and a memory 154. Memory 154 may include programs, instructions, functions, or routines for execution by processor 150, as will be described herein. In one aspect, processor 150 may receive medical data/information through an interface 160 from the various BSUs 104 and signals about patient actions from sensors 140 through interface 162. BAC 110 may unlock BAN 100 of a patient 102 to transmit medical data about the patient from the BSUs 104 and/or sensors 140 through transceiver 152 and via link 112 to wireless or mobile device 114 based upon a pre-defined patient action implemented or performed by the patient 102.

For example, processor 150 may unlock BAN 100 based upon a pre-defined patient action performed by the patient 102 and sensed by sensors 140 and may then connect BAN 100 through link 112 to wireless or mobile device 114. As an example, processor 150 may command transceiver 152 to transmit BAN medical data associated with the patient 102 via link 112 to wireless or mobile device 114. Link 112 may be a local area network (LAN), a wireless local area network (WLAN) link, or any short range network link. As examples, link 112 may be a WiFi link, a Near Field Communication link, a BLUETOOTH link, USB link, or any type of suitable local area or short range link. Further, wireless or mobile device 114 of the patient (or the wireless or mobile device of another user (e.g., helpful bystander, emergency responder, etc.)) may transmit the BAN medical data through a wireless or wired link 115 to an emergency service, as will be described in more detail. Further, it should be appreciated that device 114 may be any type of computing device which may communicate via wired or wireless links.

Examples of pre-defined patient actions will be hereinafter discussed. For example, a pre-defined patient action to unlock BAN 100 may include a patient 102 pressing against a pre-designated part of the body that includes a sensor 140. With brief additional reference to FIG. 2, some examples of pre-defined patient actions will be described. As one example, a patient 102 may press their hands 215 against the back of their head 220 for a pre-determined amount of time. The patient 102 may have internal or external sensors 140 (not shown) associated with their head 220 and hands 215 that will sense one another, and after a pre-determined amount of time, will transmit a signal to BAC 110 to unlock BAN 100.

Figure 2:
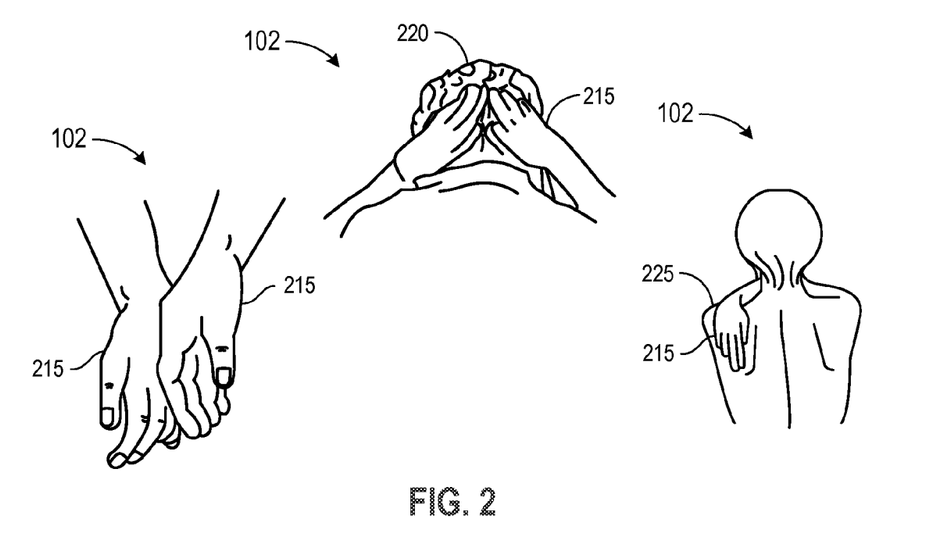
FIG. 2 is a diagram illustrating examples of pre-defined patient actions that may be used to unlock the BAN system.

As another example, a pre-defined patient action to unlock the BAN 100 may include a pre-designated body movement. For example, a patient 102 may touch the back of their hands 215 together three times to unlock BAN 100. As yet another example, the patient 102 may touch their hand 215 to the back of their shoulder 225 two times. The patient 102 may have internal or external sensors 140 (not shown) associated with their hands 215 and back 225 that will sense one another and will transmit a signal to BAC 110 to unlock BAN 100.

It should be appreciated that there are a wide variety of different types of patient actions that may be pre-defined and that may be sensed by sensors 140 as far as time and frequency to unlock the BAN 100. In particular, signals from sensors 140 may be transmitted and received by processor 150 of BAC 110, and if they match pre-defined criteria, processor 150 may unlock BAN 100 and connect BAN 100 to wireless or mobile device 114 via link 112.

It should be appreciated that pressing against a pre-designated part of the body or a pre-designated body movement related to touching hands 215 together, touching the back of the head 220, or touching the shoulder 225, are merely examples of a wide variety of different types of techniques for touching different body part and movements that may be utilized. A wide variety of different body parts, movements, and sensors may be utilized. However, the techniques should be specific enough to ensure that the BAN 100 does not unlock due to casual contact and also that the patient is aware that they are unlocking their BAN.

As to sensors 140, a wide variety of different types of internal or external sensors may be utilized at different parts of the patient's body. Examples were provided as to a patient's hands 215, a patient's head 220, patient's shoulder 220, however, as should be appreciated, any suitable part of the body may be utilized. Further, any suitable type of internal or external sensor 140 may utilized. Examples of sensors 140 may include motion sensors (e.g., accelerometers), pressure sensors, force sensors, sound sensors, vibration sensors, magnetic sensors, proximity sensors, optical sensors, electrical sensors, light sensors, laser sensors, image sensors, conductive sensors, radio sensors, position sensors, angle sensors, displacement sensors, distance sensors, speed sensors, heat sensors, temperature sensors, etc., or any type of sensor that may be utilized to identify a pre-defined patient action such as pressing against a pre-designated part of the body or identifying a pre-designated body movement.

In particular, if processor 150 of BAC 110 identifies a pre-defined patient action from a sensor 140 such as a patient pressing against a pre-designated part of the body or a pre-designated body movement, processor 150 will unlock BAN 100 such that BAN medical data is transmitted via link 112 to wireless or mobile device 114. Wireless or mobile device 114 may then transmit the BAN medical data via link 115 to another entity such as an appropriate emergency service. Although wireless or mobile device 114 may transmit the BAN medical data via link 115 to an appropriate emergency service, it may also transmit the BAN medical data to other entities, as will be described.

Additionally, in one aspect, if a patient 102 is incapable of performing a pre-defined action then BAN 100 may be automatically unlocked. For example, if the patient 102 is unconscious or severely injured, an appropriate BSU 104 may transmit appropriate data to processor 150 of BAC 110 such that processor 150 unlocks the BAN 100 and transmits the BAN medical data via link 112 to a wireless or mobile device 114, at which point, the wireless or mobile device 114 may transmit the BAN medical data via link 115 to another entity such as an appropriate emergence service. As a particular example, processor 150 may automatically unlock the BAN 100 based upon a pre-defined body change of the patient 102 identified by one of the BSUs 104. For example, ECG sensor 128 may detect a major heart abnormality, blood pressure sensor 130 may detect a severe decrease or increase in blood pressure, toxin sensor 132 may detect a huge amount of toxins. All of these are examples of a pre-defined body change of a patient that may be detected by a BSU 104 and a corresponding signal from the BSU 104 may be transmitted via I/F 160 to BAC 110, which under control of processor 150, may unlock the BAN 100, transmit the patient's BAN medical data to wireless or mobile device 114 via link 112, and wireless or mobile device 114 may transmit the patient's BAN medical data to an appropriate emergency service via link 115. It should be appreciated that any type of medical condition that renders a patient unconscious, incapacitated, or severely injured may be detected by an appropriate BSU 104 and the BAN 100 automatically unlocked for the patient 102.

As previously described, according to one aspect, after processor 150 of BAC 110 unlocks the BAN 100, the medical data from the BAN 100 may be transmitted through transceiver 152 via link 112 to wireless or mobile device 114 and the wireless or mobile device 114 may transmit the BAN medical data via wireless link 115 (e.g., a cellular network) to an emergency service. For example, the wireless or mobile device 114 may transmit their BAN medical data through an appropriate emergency call (e.g., x911) to an appropriate emergency service to request medical assistance (e.g., an ambulance, paramedic, fire department, police response, etc.).

Figure 3A:
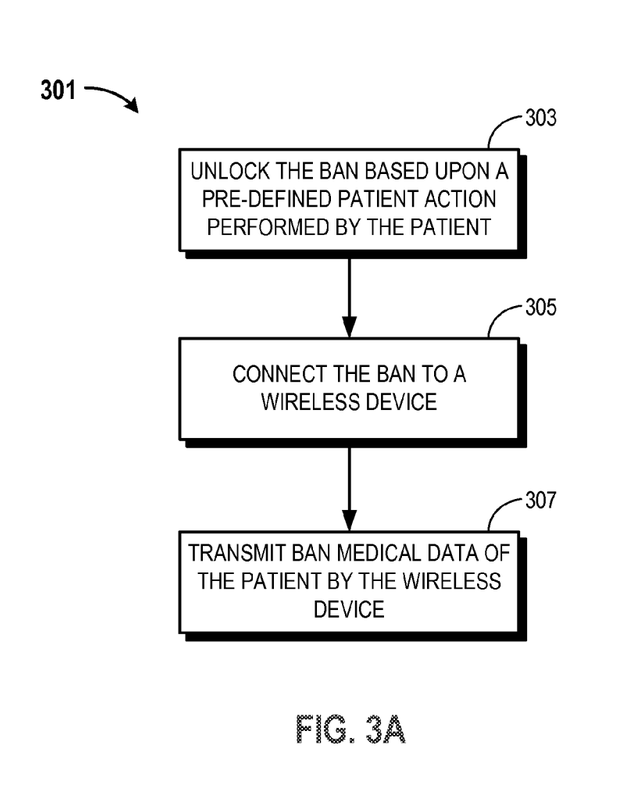
FIG. 3A is a flow diagram that illustrates a process to unlock the BAN system.

With brief reference to FIG. 3A, a flow diagram illustrates a process 301 that may be executed by BAN 100. At block 303, BAN 100 is unlocked based upon a pre-defined patient action performed by the patient 102. For example, a patient may press against a pre-designated part of the body or perform a pre-designated body movement as previously described with reference to FIG. 2. Next, at block 305, the BAN 100 is connected a wireless device. For example, as previously described with reference to FIGS. 1A and 1B, processor 150 of BAC 110 may unlock BAN 100 such that the BAN medical data of the patient is transmitted from transceiver 152 via link 112 to the wireless or mobile device 114. Further, at block 307, the BAN medical data of the patient is transmitted by the wireless device. As an example, as previously described, wireless or mobile device 114 may then transmit the BAN medical data via link 115 to another entity such as an appropriate emergency service.

Figure 3B:
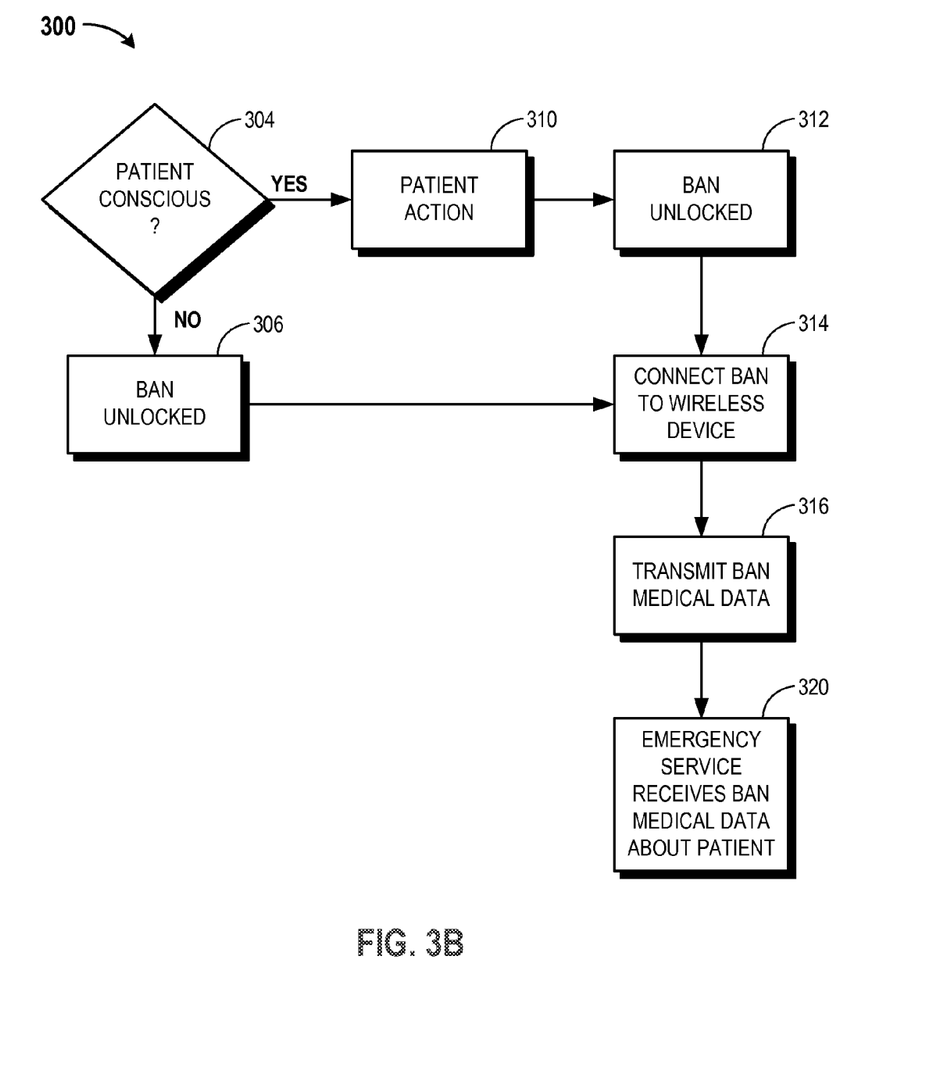
FIG. 3B is a flow diagram that illustrates another process to unlock the BAN system.

With brief reference to FIG. 3B, a flow diagram illustrates process 300 that may be performed or executed by BAN 100. At decision block 304, based upon data received from BSUs 104, processor 150 of BAC 110 may determine if the patient is conscious. If not, BAN 100 is unlocked (block 306) and the process 300 moves to block 314, as will be hereinafter described. If the patient is conscious, then BAC 110 requires a pre-defined patient action (block 310) to unlock BAN 100, such as pressing against a pre-designated part of the body or a pre-designated body movement (as previously described), then BAN 100 is unlocked (block 312). BAC 110 may then connect BAN 100 to wireless or mobile device 114 via link 112 (block 314) and transmits the patient's BAN medical data to the wireless or mobile device 114 (block 316). Next, another entity such as an emergency service may receive the BAN medical data about the patient via link 115 from a transmission by the wireless or mobile device 114 (block 320). It should be appreciated that wireless or mobile device 114 may be a patient's wireless device, a helper's wireless device, or an emergency responder's wireless device. Further, it should be appreciated that device 114 may be any type of computing device which may communicate via wired or wireless links.

As an example, the patient's wireless or mobile device 114 may start sending BAN medical data to an emergency service (e.g., via a x911 call) when the BAN 100 is unlocked. This may alert the emergency service of the patient's medical emergency and medical condition and allow emergency responders (e.g., paramedics) to access the patient's BAN medical data and identify data while en-route to the patient saving valuable time and aiding the medical responders once they arrive. Further, the emergency service can provide medical advice to the patient or a helper through the wireless or mobile device as to how to best respond to their current medical condition.

Figure 4:
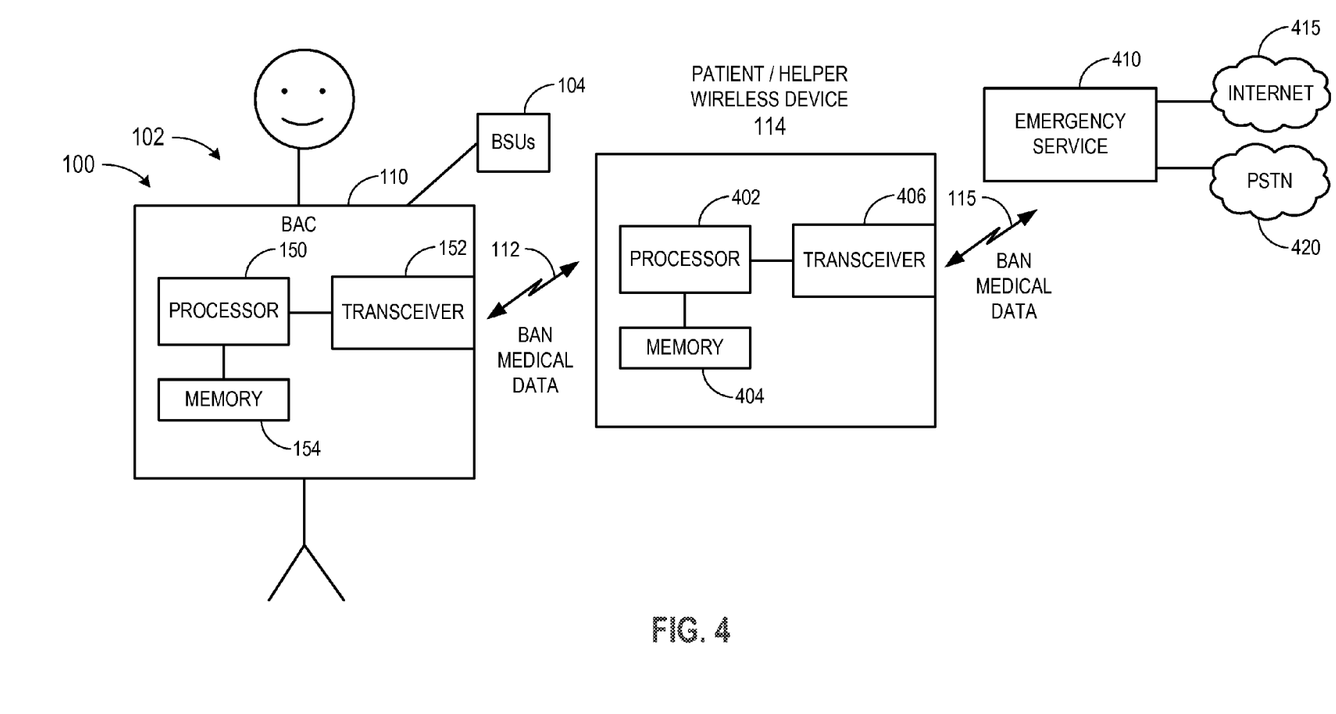
FIG. 4 is a diagram illustrating a patient or helper utilizing their wireless device to transmit BAN medical data.

Turning now to FIG. 4, a block diagram illustrating a patient or helper utilizing their wireless or mobile device 114 to transmit BAN medical data is shown. As previously described, a patient 102 may unlock their BAN 100 by a pre-defined patient action, such as pressing against a pre-designated part of the body or a pre-designated body movement. Also, BAN 100 may also be unlocked if the patient is unconscious and incapable of performing a pre-defined patient action (e.g., unconscious) or if a pre-defined body change of the patient occurs as identified by one of BSUs 104 (e.g., low blood pressure, low heart rate, etc.).

In particular, when one or more of these unlocking features or activities occur, as identified by processor 150 of BAC 110, processor 150 through transceiver 152 transmits the BAN medical data via link 112 to wireless or mobile device 114. Wireless or mobile device 114 may be the wireless or mobile device of the patient, a helper, or any other user. Based upon the receipt of the BAN medical data via link 112, wireless or mobile device 114 under the control of processor 402 may recognize the BAN medical data and may command transceiver 406 to transmit the BAN medical data via a link 115 to another entity such as an emergency service 410. Memory 404 may include programs, instructions, functions, or routines for execution by processor 402. It should be appreciated that wireless or mobile device 114 may be a cell phone, tablet, smart phone, laptop computer, PDA, or any sort of computing device with wireless or wired connectivity. Also, common features of a wireless or mobile device, such as, user interfaces, display devices, etc., have not been described herein for brevity's sake, but are apparent to those of skill in the art.

As one example, wireless or mobile device 114 may include an application program, that, upon receipt of the BAN medical data from the BAC 110 of the BAN 100 via link 112, may provide an emergency response option, such that if a patient or helper selects the emergency response option (e.g., pushing a button on the user interface such as through a keypad or on the display device), wireless or mobile device 114 under the control of processor 402 transmits the BAN medical data and patient information through the transceiver 406 via wired or wireless link 115 to an emergency service 410. As an example, this may be similar to a x911 call. In one aspect, the x911 call may pre-programmed into the wireless or mobile device 114 as part of the application program. As another example, the wireless or mobile device 114 may simply transmit the BAN medical data and patient information via link 115 to emergency service 410 upon receipt of the BAN medical data automatically without a user selecting the emergency response option.

Emergency service 410 may be a government or private emergency service (e.g., a Public Safety Answering Point (PSAP) reachable via a x911 call or another suitable call) that controls: ambulance service, medical service, police service, fire department service, etc. The emergency service 410 may further be connected through the Internet 415 and a public switched telephone network (PSTN) 420 to other entities, data sources, etc. Emergency service 410 may instruct an emergency responder (e.g., an ambulance, paramedic, fire engine, police, etc.) to go the patient 102 and provide medical assistance. Further, the emergency service 410 may provide the emergency responder with the patient's BAN medical data, position information, as well as additional medical data about the patient. This allows the emergency responder to access the patient's health and identity data while en-route to the patient, saving valuable time, and may help the medical responder once they arrive. Additionally, the emergency service 410 may transmit medical advice to the wireless or mobile device 114 of patient/helper to help the patient/helper to deal with the medical emergency while they await the emergency responder. Further, it should be appreciated that device 114 may be any type of computing device which may communicate via wired or wireless links.

Figure 5:
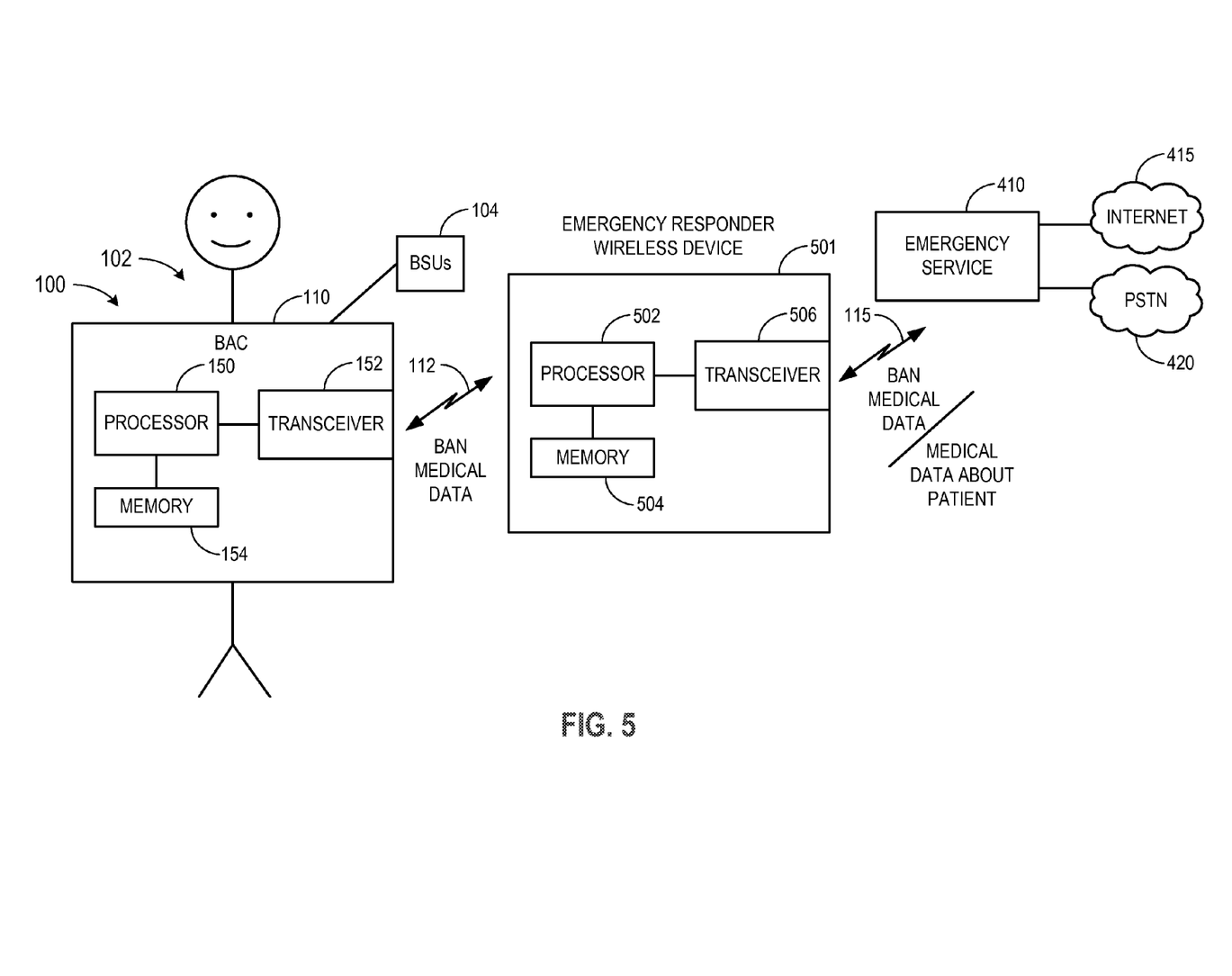
FIG. 5 is a diagram illustrating the use of a wireless device by an emergency responder.

With additional reference to FIG. 5, once the emergency service 410 has been contacted, and the emergency responder has been sent en-route to the patient 102, the emergency responder's device 501, such as a wireless device or a mobile device, may include a processor 502, memory 504, and transceiver 506, may receive via link 115 from the emergency service 410, the patient's BAN medical data, position information, as well as additional medical data about the patient. This allows the emergency responder to access the patients' health and identity data while en-route to the patient, saving valuable time, and may help the medical responder once they arrive. Additional medical information about the patient may be provided to the wireless or mobile device 501 of the medical responder via wireless or wired link 115 that the emergency service 410 acquires through the Internet 415 or other networks from hospital, doctors, medical networks, etc., that relate to the medical history of the patient 102. It should be appreciated that device 501 may be any type of computing device with or without wireless capabilities, and in one embodiment, may be a medical device.

Further, once the emergency responder arrives to patient 102, the BAN medical data of the patient 102 may be transmitted via link 112 directly to the wireless or mobile device 501 of the emergency responder such that the processor 502 can process the BAN medical data information about the patient and can display the BAN medical information to the emergency responder. It should be appreciated that wireless or mobile device 501 of the emergency responder may also be a medical device that utilizes the BAN medical information for medical device functions. The wireless or mobile device 501 of the emergency responder may transmit the BAN medical data of the patient to a medical data server 612 (see FIG. 6) of a hospital, a medical service provider (e.g., a doctor), or a medical network. For example, the medical data sever 612 may be a server of a nearby hospital or a medical network that has medical data and other information (e.g., identity information, contact information, etc.) about the patient 102. Additionally, the wireless or mobile device 501 of the emergency responder may further receive medical data and/or instructions about how to best medically treat the patient from the medical data server 612.

Figure 6:
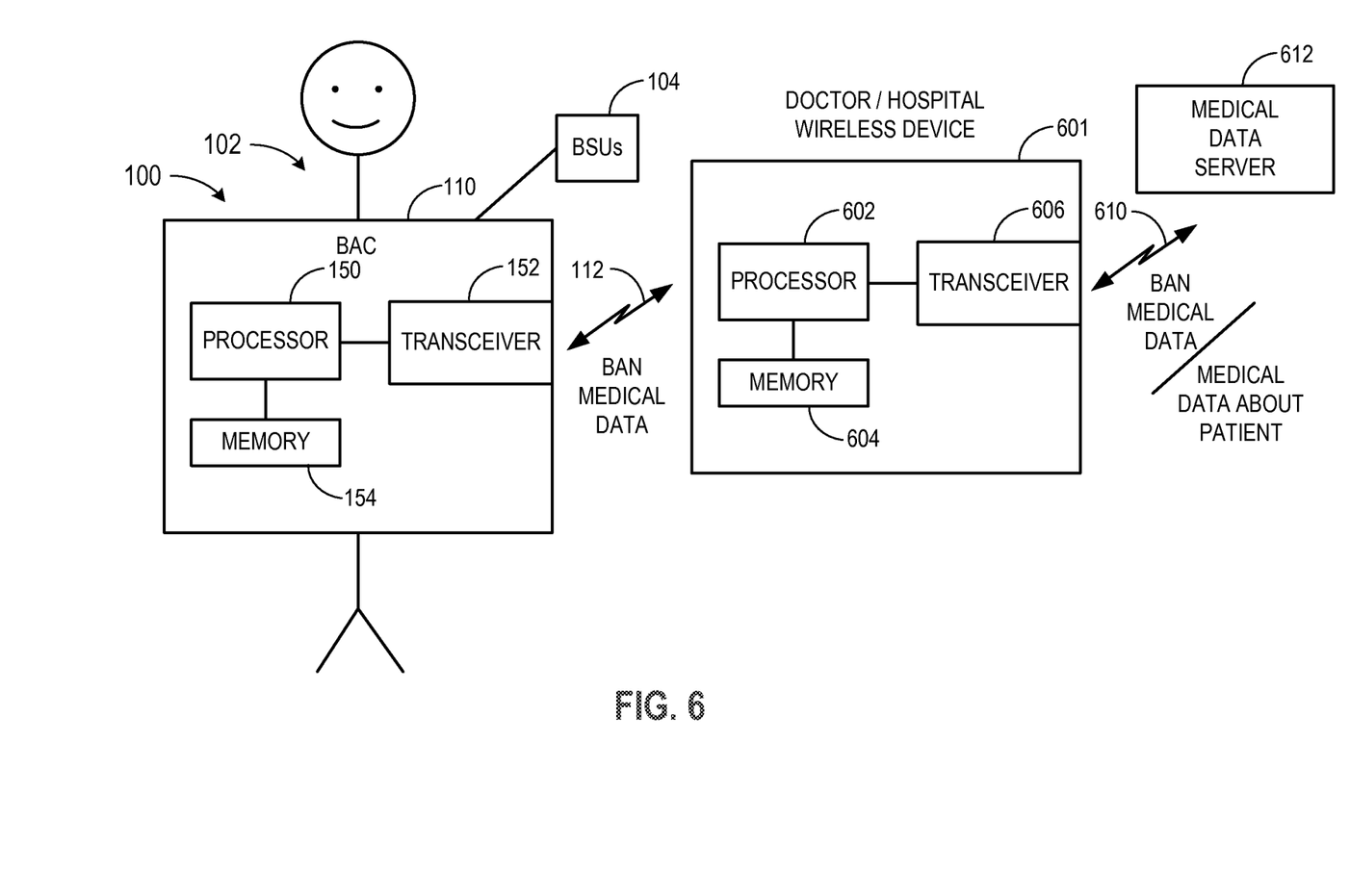
FIG. 6 is a diagram illustrating the use of a wireless device by a medical support person.

With reference to FIG. 6, according to yet another aspect, the BAN 100 of a patient 102 may be connected to a device 601 of medical support personnel (e.g., a nurse at a hospital, a doctor at a doctor's office, etc.). The device 601 may be a wireless, mobile, or wired device and may include a processor 602, memory 604, and a transceiver 606. For example, the device 601 may be a cell phone, laptop, tablet, personal computer, personal digital assistant (PDA), etc., or may be a medical device with or without wireless capabilities. It should be appreciated that device 601 may be any type of device with or without wireless capabilities, and in one embodiment, may be a medical device. As previously described, the patient 102 may unlock the BAN 110 based upon a pre-defined patient action such as pressing against a pre-designated part of the body or a pre-designated body movement. The device 601 may receive the patient's BAN medical data via link 112 through transceiver 606 and through transceiver 606 may transmit the patient's BAN medical data through a link 610 to a medical data server 612 associated with the hospital, the doctor's office, or a medical network associated with the patient. The device 601 of the medical support personnel may further receive medical data via link 610 from the medical data server 612. In this way, the medical support personnel utilizing a device 601 may receive medical data and other information (e.g., identity information, contact information, etc.) about the patient. Further, in the example in which the device 601 is a wireless medical device, the BAN medical data of the patient may 102 be inputted into the wireless medical device.

As an example, a nurse at a hospital utilizing a medical device 601 may receive BAN medical data via link 112 from the BAC 110 of a patient such that medical device 601 under the control of processor 602 may utilize the BAN medical data for monitoring functions, such as: monitoring blood pressure, monitoring heart rate, etc. Further, medical device 601 may transmit via transceiver 606, through link 610, the BAN medical data about the patient to the medical data server 612 at the hospital and the medical device 601 may further receive medical data about the patient from the medical data server 612. It should be appreciated, that these links for the medical device may be wired or wireless. As another example, a patient may visit a doctor at the doctor's office, unlock their BAN 100 based upon a pre-defined patient action, and the BAN medical data via link 112 may provide to the doctor's device 601 (e.g., a laptop) access to the patient's current BAN medical data as measured by the BSUs 104, a log of past medical data measured by the BAN 100, as well as other information about the patient, such that the doctor can analyze the patient's health.

As to security features for doctor, hospital, etc., the patient 102 may still unlock their BAN 100 based upon a pre-defined patient action or a pre-designated body movement, as previously described, to ensure security. Additionally, after this secure opening, the doctors, nurses, etc. may utilize a new shared key or a previously utilized shared key with the BAN 100 of the patient. In some aspects, a key may be displayed on the BCU. Further, access to the BAN 100 may be based on the link 112 and may be limited by location and proximity to device 601. The patient can also re-lock their BAN 100 at any time. Different levels of access may also be provided such as: single person access (e.g., only to a doctor), group access or multiple person access (e.g., to visiting nurses in proximity), or completely open access to anyone in proximity. Additionally, different types of access to the BAN may be provided, such as: read/write access (e.g., only doctors) or read access only (e.g., to nurses), etc. It should be appreciated that a wide variety of different types of access may be employed.

Thus, a system, method, and apparatus are described in which a BAN 100 may be unlocked if a patient 102 is capable of performing a pre-defined patient action (i.e., the patient is conscious). An example of this may be a patient 102 pressing against a specific part of the body for a pre-determined period of time or the patient 102 making a specific pre-designated body movement (e.g., touching the backs of the hands together). However, if the patient 102 is unable to perform the pre-defined patient action (e.g., the patient is unconscious or has severe body problems as measured by the BSUs 104) then the consent to unlock the BAN 100 may be implied and the BAN 100 may automatically unlock itself. Further, because wireless or mobile devices (e.g., cell phones) are increasingly prevalent, they may be utilized in conjunction with the BAN 100. For example, a patient's wireless or mobile device (or that of a helpful bystander) may start sending the BAN's medical data to an emergency service (e.g., via x911) when the BAN 100 is unlocked and the emergency service may send an emergency responder to the patient 102. Further, this may allow emergency responders (e.g., paramedics) to access the patient's BAN medical data and other health and identity data and prepare while en-route to the patient saving valuable time and this can help medical responders once they arrive. Moreover, medical advice can be given to the patient and/or helpers while the medical responders are en-route to them.

It should be appreciated that embodiments of the invention previously described may be performed in conjunction with the execution of instructions by processors (e.g., processors of the BAC 110, the patient/helper's wireless or mobile device 114, the emergency responder's wireless or mobile device 501, the doctor/hospital's device 601, etc.), and/or other circuitry and/or other devices. Particularly, this circuitry, including but not limited to processors, may operate under the control of a program, routine, or the execution of instructions to execute methods or processes in accordance with embodiments of the invention. For example, such a program may be executed in firmware or software (e.g. stored in memory and/or other locations) and may be executed by processors and/or other circuitry. Further, it should be appreciated that the terms processor, microprocessor, circuitry, controller, etc., refer to any type of logic or circuitry capable of executing logic, commands, instructions, software, firmware, functionality, etc.

Further, the BAC 110, the patient/helper's wireless or mobile device 114, the emergency responder's wireless or mobile device 501, the doctor/hospital's device 601, emergency service 415, medical data server 612, etc., may communicate via one or more wireless communication links (e.g., links 112, 115, 610, etc.) that are based on or otherwise support any suitable wireless communication technology or may communicate via wired communication links. For example, in some aspects the wireless or mobile devices may associate with a network. In some aspects the network may comprise a body area network or a personal area network (e.g., an ultra-wideband network). In some aspects the network may comprise a local area network or a wide area network. A wireless or mobile device may support or otherwise use one or more of a variety of wireless communication technologies, protocols, or standards such as, for example, GSM, CDMA, TDMA, OFDM, OFDMA, WiMAX, and Wi-Fi. Similarly, a wireless or mobile device may support or otherwise use one or more of a variety of corresponding modulation or multiplexing schemes. A wireless or mobile device may thus include appropriate components (e.g., air interfaces) to establish and communicate via one or more wireless communication links using the above or other wireless communication technologies. For example, a device may comprise a wireless transceiver with associated transmitter and receiver components (e.g., a transmitter and a receiver) that may include various components (e.g., signal generators and signal processors) that facilitate communication over a wireless medium. As is well known, a wireless or mobile device may therefore wirelessly communicate with other mobile devices, cell phones, other wired and wireless computers, Internet web-sites, etc.

The teachings herein may be incorporated into (e.g., executed within or performed by) a variety of apparatuses (e.g., devices). For example, one or more aspects taught herein may be incorporated into a phone (e.g., a cellular phone), a smart phone, a tablet, a laptop computer, a personal data assistant ("PDA"), an entertainment device (e.g., a music or video device), a headset (e.g., headphones, an earpiece, etc.), a microphone, a medical device (e.g., a biometric sensor, a heart rate monitor, a pedometer, an EKG device, etc.), a computer, a server, a point-of-sale device, a hearing aid, a set-top box, or any other suitable device.

In some aspects a wireless or mobile device may comprise an access device (e.g., a Wi-Fi access point) for a communication system. Such an access device (also referred to as a base station) may provide, for example, connectivity to another network (e.g., a wide area network such as the Internet or a cellular network) via a wired or wireless communication link. Accordingly, the access device may enable another device (e.g., a Wi-Fi station) to access the other network or some other functionality. In addition, it should be appreciated that one or both of the devices may be portable or, in some cases, relatively non-portable.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be performed as electronic hardware, computer software, or combinations of both. To clearly illustrate this interchangeability of hardware and software, various illustrative components, blocks, modules, circuits, and steps have been described above generally in terms of their functionality. Whether such functionality is performed as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be executed or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method, process, routine, or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be performed in hardware, software, firmware, or any combination thereof. If performed in software as a computer program product, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A non-transitory computer-readable medium including code that, when executed by a processor, causes the processor to:
   unlock a body area network (BAN) based upon a pre-defined patient action performed by a patient, wherein the pre-defined patient action to unlock the BAN includes pressing against a pre-designated part of the body;
   connect the BAN to a wireless device; and
   process information from the BAN using the wireless device.

2. The computer-readable medium of claim 1, wherein, the BAN includes a body area controller (BAC) and one or more body sensor units (BSUs).

3. The computer-readable medium of claim 1, further comprising code to transmit BAN medical data of the patient by the wireless device.

4. The computer-readable medium of claim 3, wherein the BAN is connected to a wireless device of the patient and the BAN medical data of the patient is transmitted from the wireless device of the patient to an emergency service.

5. The computer-readable medium of claim 3, wherein the BAN is connected to a wireless device of a helper and the BAN medical data of the patient is transmitted from the wireless device of the helper to an emergency service.

6. The computer-readable medium of claim 3, wherein the BAN is connected to a wireless device of an emergency responder and the BAN medical data of the patient is transmitted from the wireless device of the emergency responder to a medical data server.

7. The computer-readable medium of claim 6, wherein the wireless device of the emergency responder further receives medical data about the patient from the medical data server.

8. An apparatus comprising:
means for unlocking a body area network (BAN) based upon a pre-defined patient action performed by the patient, wherein the pre-defined patient action to unlock the BAN includes pressing against a pre-designated part of the body;
means for connecting the BAN to a wireless device; and
means for processing information from the BAN using the wireless device.

9. The apparatus of claim 8, wherein, the BAN includes a body area controller (BAC) and one or more body sensor units (BSUs).

10. The apparatus of claim 8, wherein, BAN medical data of the patient is transmitted by the wireless device.

11. The apparatus of claim 10, wherein the BAN is connected to a wireless device of the patient and the BAN medical data of the patient is transmitted from the wireless device of the patient to an emergency service.

12. The apparatus of claim 10, wherein the BAN is connected to a wireless device of a helper and the BAN medical data of the patient is transmitted from the wireless device of the helper to an emergency service.

13. The apparatus of claim 10, wherein the BAN is connected to a wireless device of an emergency responder and the BAN medical data of the patient is transmitted from the wireless device of the emergency responder to a medical data server.

14. The apparatus of claim 13, wherein the wireless device of the emergency responder further receives medical data about the patient from the medical data server.

15. A apparatus comprising:
a transceiver; and
a processor coupled to the transceiver, the processor configured to:
unlock a body area network (BAN) based upon a pre-defined patient action performed by the patient, wherein the pre-defined patient action to unlock the BAN includes pressing against a pre-designated part of the body; and
connect the BAN to a wireless device through the transceiver, wherein information from the BAN is processed using the wireless device.

16. The apparatus of claim 15, wherein, the BAN includes a body area controller (BAC) and one or more body sensor units (BSUs).

17. The apparatus of claim 15, wherein, BAN medical data of the patient is transmitted by the wireless device.

18. The apparatus of claim 17, wherein the BAN is connected to a wireless device of the patient and the BAN medical data of the patient is transmitted from the wireless device of the patient to an emergency service.

19. The apparatus of claim 17, wherein the BAN is connected to a wireless device of a helper and the BAN medical data of the patient is transmitted from the wireless device of the helper to an emergency service.

20. The apparatus of claim 17, wherein the BAN is connected to a wireless device of an emergency responder and the BAN medical data of the patient is transmitted from the wireless device of the emergency responder to a medical data server.

21. The apparatus of claim 17, wherein the wireless device of the emergency responder further receives medical data about the patient from the medical data server.

* * * * *